(12) United States Patent  (10) Patent No.: US 7,385,176 B2
Pfeiffer et al.                (45) Date of Patent:    Jun. 10, 2008

(54) CALIBRATION REFLECTOR DEVICE, SENSOR ARRANGEMENT, AND METHOD FOR STERILE PACKAGING OF A FIBER-OPTIC SENSOR ARRANGEMENT

(75) Inventors: Ulrich J. Pfeiffer, Munich (DE); Daniel Moulas, Pfaffing (DE)

(73) Assignee: Pulsion Medical Systems AG, Munich (DE)

( * ) Notice: Subject to any disclaimer, the term of this patent is extended or adjusted under 35 U.S.C. 154(b) by 48 days.

(21) Appl. No.: 11/281,643

(22) Filed: Nov. 17, 2005

(65) Prior Publication Data

US 2006/0138314 A1    Jun. 29, 2006

(30) Foreign Application Priority Data

Nov. 17, 2004   (EP)   ................... 04105835

(51) Int. Cl.
  *G01J 1/04*   (2006.01)
  *G01J 1/42*   (2006.01)
  *G01J 5/08*   (2006.01)
(52) U.S. Cl. ............................ 250/227.14; 250/559.11; 600/332; 600/342; 385/12; 385/15; 385/88; 385/92
(58) Field of Classification Search ................ 250/239, 250/559.11, 214.1, 227.11, 227.24, 227.2, 250/227.14, 363.02, 363.04, 363.05; 600/332, 600/342; 385/12, 13, 15, 53, 88, 90, 92, 385/94

See application file for complete search history.

(56) References Cited

U.S. PATENT DOCUMENTS

| 4,050,450 A | 9/1977 | Polanyi et al. |
| 4,981,355 A | 1/1991 | Higgins |
| 5,175,977 A * | 1/1993 | Crawford et al. ............. 53/399 |
| 5,305,744 A | 4/1994 | Pfeiffer et al. |
| 5,365,925 A | 11/1994 | Lee |
| 5,710,856 A * | 1/1998 | Ishii et al. .................. 385/146 |
| 2004/0064021 A1 * | 4/2004 | Pfeiffer ....................... 600/341 |

FOREIGN PATENT DOCUMENTS

EP     0561126    9/1993

* cited by examiner

*Primary Examiner*—Georgia Y. Epps
*Assistant Examiner*—Francis M Legasse, Jr.
(74) *Attorney, Agent, or Firm*—Collard & Roe, P.C.

(57) ABSTRACT

A tube-like reflector insert for a sensor is located in a rigid, light-absorbing sleeve that is closed on one side, and forms a two-part reflector body with the sleeve. A nut is glued onto the open side of the sleeve to enclose the reflector insert. The intravasal part of the sensor is guided in a protective tube having connector threads glued on on both sides. This protective tube is screwed onto the Y connector piece and the reflector sleeve with the nuts. The tip of the sensor is inserted with slight play into the sensor cavity of the reflector insert. The play ensures that sterilization gas can reach all of the intravasal surfaces. The reflector is attached to the sensor via a screw connection outside of the intravasal region, which ensures that the intravasal sensor part is not exposed to clamping stress. Free access for sterilization gas is possible at all intravasal surfaces of the sensor.

31 Claims, 2 Drawing Sheets

CALIBRATION REFLECTOR DEVICE, SENSOR ARRANGEMENT, AND METHOD FOR STERILE PACKAGING OF A FIBER-OPTIC SENSOR ARRANGEMENT

BACKGROUND OF THE INVENTION

1. Field of the Invention

The present invention relates to a calibration reflector device for fiber-optic sensors, as well as a sensor arrangement equipped with such a calibration reflector device, particularly for medical use.

2. The Prior Art

Fiber-optic sensors are known in many different embodiments, and are used in medicine, for example, for intravasal measurement of the oxygen saturation in blood. In order to prevent infections, which often have serious consequences, up to and including lethal sepsis, the intravasal part of the sensor must be kept sterile. For other optical measurements to be carried out in situ, including non-medical measurements, the sensor parts to be guided to the measurement site usually must be protected from contamination.

In order to obtain usable measurement results, sensor calibration is generally necessary before the measurement is carried out. For this purpose, calibration reflectors are usually used. These possess reflection properties that are as well-defined as possible. The proportion of the light that is emitted from one or more emitter fibers of the sensor, which portion is reflected by the calibration reflector and detected by the measurement fiber or measurement fibers, serves as the reference value for the actual measurements.

Calibration reflector devices and sensor arrangements of the type stated initially are known from U.S. Pat. No. 4,050,450 and European Patent No. 0 561 126 B1. Usually, conventional calibration reflector devices are clamped to the tip of the sensors to be calibrated. Since the plastics used for the sensors tend to cold-flow under stress, clamping results in permanent deformation, particularly in the case of thin sensors. This deformation interferes both with the introduction of the sensors by way of insertion mechanisms, and with the measurement. Another problem is that no sterilization gas can reach the clamped surfaces. The sensors therefore usually have to be sterilized using gamma rays. However, the gamma radiation used changes the optical properties of the sensors.

SUMMARY OF THE INVENTION

It is therefore an object of the invention to create a calibration reflector device as well as a sensor arrangement equipped therewith, which prevents harmful deformations of the sensor in the region of the tip, and does not impair its ability to be sterilized. Furthermore, it is another object of the invention to guarantee reliable and simple handling, particularly in a clinical setting. It is a further object of the invention to eliminate outside light during the calibration process. It is yet a further object of the invention to create a method for sterile packaging of a fiber-optic sensor arrangement, which can be used without the use of gamma rays.

This object is accomplished by a calibration reflector device for a fiber-optic sensor, comprising a rigid reflector body, which has a sensor cavity for accommodating a sensor end and being acccessible from one access side, as well as connection means for reversibly connecting a connector piece to the access side. The connection means are disposed radially outside a free space in the closed position, for passing the sensor through. The cross-sectional expanse of the free space is at least as large as the cross-section of the sensor cavity.

According to the invention, a rigid sheath arrangement in the shape of a reflector body is therefore provided for the sensitive sensor tip. This arrangement prevents the collapsing and bending stresses that disrupt the calibration measurement. A radial play is provided, which makes it possible to reach the intravasal sensor part with sterilization gas. A low radial play of less than 25%, preferably less than 10% of the sensor diameter in the region of the intravasal part is particularly advantageous, in order to protect the intravasal part of the sensor from bending and tilting.

The surface of the sensor cavity is preferably textured, for example in the form of roughening and/or ribbing of the surface and/or in the form of a star-shaped or otherwise profiled cavity cross-section. This texturing often improves the distribution of the sterilization gas over the surfaces to be sterilized. Furthermore, disruptive light reflections at the surface are prevented in this manner. An improvement in the distribution of the sterilization gas over the surfaces to be sterilized can often be achieved by a slightly oval cross-section of the sensor cavity, with a round sensor cross-section.

Usually, the cross-section of the sensor cavity as well as the cross-section of the sensor are substantially uniform over the majority of their respective (axial) length. The sensor cavity thus may be substantially tubular.

The term "intravasal part" means the part of a fiber-optic sensor that leads to the measurement site, which part must be protected against contamination and/or sterilized for use of the sensor.

The connection of the reflector body with the sensor by way of connection means that are disposed radially outside of a free space, the cross-section of which is sufficiently large to allow clamp-free placement of the intravasal sensor part, instead of the conventional clamp connection, also contributes to the sterilizability with flushing gas. Furthermore, because of the absence of clamp sites in the vicinity of the sensor tip, material deformation that impairs the measurement accuracy is avoided. Appropriate connection means can be implemented, for example, as screw connections, for example by means of commercially available Luer lock nuts and threads, a bayonet connection, clamping outside of the intravasal sensor part, or the like.

The cross section of the free space may be substantially uniform over at least part of its respective (axial) length.

The extension piece provided between connection devices and reflector body, preferably axially, protects the region of the intravasal sensor part that does not lie within the sensor cavity. Here again, a radial play is provided (preferably somewhat greater than the radial play in the sensor cavity), in order to allow flushing with sterilization gas as well as simple retraction of the sensor. The inside surface of the extension piece can be configured in similar manner as the sensor cavity interior. It is advantageous in many respects if the extension piece is configured in flexible manner, preferably in tube-like manner.

If the sensor cavity is disposed in a flexible, tube-like reflector insert, such as made of silicone or polyurethane, this insert can advantageously be embedded in a pipe-like sheathing and/or a sufficiently rigid region of the blister pack that is preferably provided (which can therefore also function as a reinforcing sheathing in the terminology selected here), in order to form the rigid reflector body and to guarantee the avoidance of any sensor bending that would influence the reflection properties, according to the invention.

The sheathing preferably made from a material that is impermeable to light or infrared radiation in the (wavelength) working range of the sensor.

The preferably black sheathing offers reliable protection against scattered light impacting the reflector, as well as the thin-walled intravasal part of the sensor.

The rigid embodiment of the reflector body, the play of the sensor in the sensor cavity, as well as an advantageous configuration of the blister pack that is preferably provided, also allow retraction of the sensor from the reflector body, with little exertion of force, without bending or stretching the sensor.

In order to prevent the sensor end from being pulled out of the reflector body before the calibration, an insertion depth of 20-60 mm, particularly preferably 25-50 mm, has proven to be advantageous. A free axial length of the sensor cavity beyond the sensor tip of at least ten times, preferably at least twenty times the root of the cross-sectional area of the sensor cavity, i.e. of the intravasal sensor part, is preferred. In the case of a circular cross-section, this is slightly less than ten times or twenty times the diameter.

The blister pack that is preferably provided also permits implementation of a system that is particularly robust, user-friendly, and self-explanatory, and therefore avoids user errors.

Using embodiments of the invention that are configured appropriately, it is possible to perform the calibration procedure and introduction of the sensor, for example into a central vein catheter, under sterile conditions, even by a person acting alone.

Thus, it is particularly advantageous for sterile handling of the sensor after the blister pack has been opened, and during calibration, to place the plug connector of the sensor, which is preferably provided, in the immediate vicinity of a tear-open tab or other tear-open aid that is preferably provided, and to provide a marking or delimitation line up to which the film, fiber non-woven layer (for example Tyvek from DuPont) or the like is supposed to be torn open, in order to be able to remove the plug connector. In this way, the remaining part of the sensor is still protected by the blister pack.

In order to protect the connector piece, which can be configured, for example, as a conventional Y connector, from falling out, it is advantageous if a suitable clamp or strain relief is provided in the blister pack.

An additional sheath, which protects the part of the sensor that must be kept sterile and also the connector piece from contamination even after complete removal from the blister pack, can be particularly advantageous.

The sensor preferably has a lumen or several lumina, and can be configured as a catheter.

The sensors are preferably configured to be particularly slim, the intravasal part of which has a maximal cross-sectional diameter of 1 mm or less.

The invention also comprises a method for sterile packaging of a fiber-optic sensor arrangement, which comprises an intravasal part and a connector piece having a flushing connector, comprising the following steps:

making available a rigid reflector body that has a sensor cavity into which the intravasal part of the sensor can be introduced with radial play, pnserting the free end of the intravasal part of the sensor into the sensor cavity, producing a releasable connection of the connector piece with the reflector body, placing the sensor arrangement into a blister pack, sterilizing with a sterilization gas, and closing the blister pack.

Generally, any variant of the invention described or indicated within the framework of the present application can be particularly advantageous, depending on the economic and technical conditions in an individual case. Individual characteristics of the embodiments described are interchangeable or can be combined with one another, unless something is stated to the contrary, or to the extent that this is fundamentally possible to implement technically.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention. In this connection, the drawings are purely schematic representations and not drawn to scale.

In the drawings, wherein similar reference characters denote similar elements throughout the several views.

DETAILED DESCRIPTION OF THE PREFERRED EMBODIMENT

Figure 1:
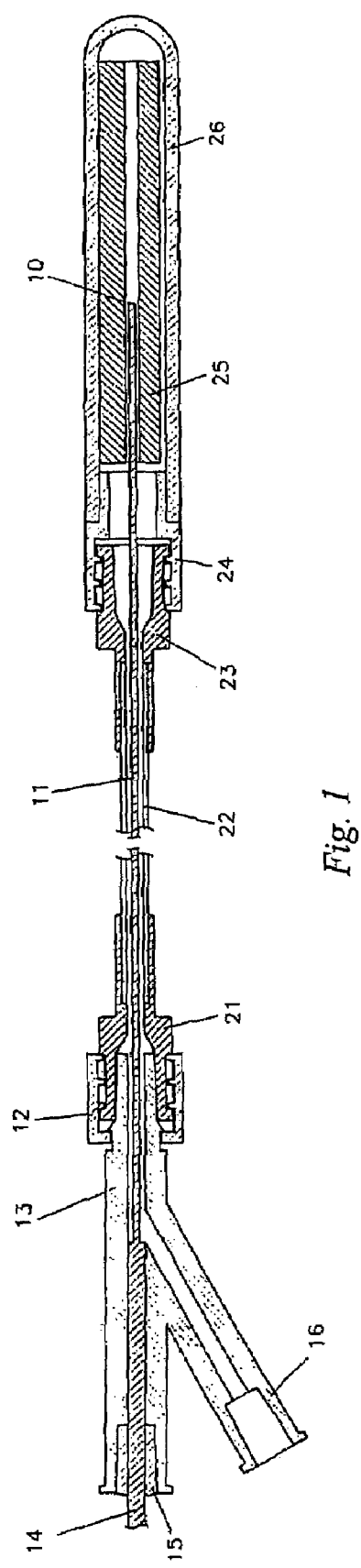
FIG. 1 shows, as a longitudinal cross-section, a sensor arrangement according to the invention, having a fiber-optic sensor and a calibration reflector device according to the invention, interrupted in the region of the extension piece configured as a protective tube, to make the illustration clear and for the drawing page format.
Figure 2:
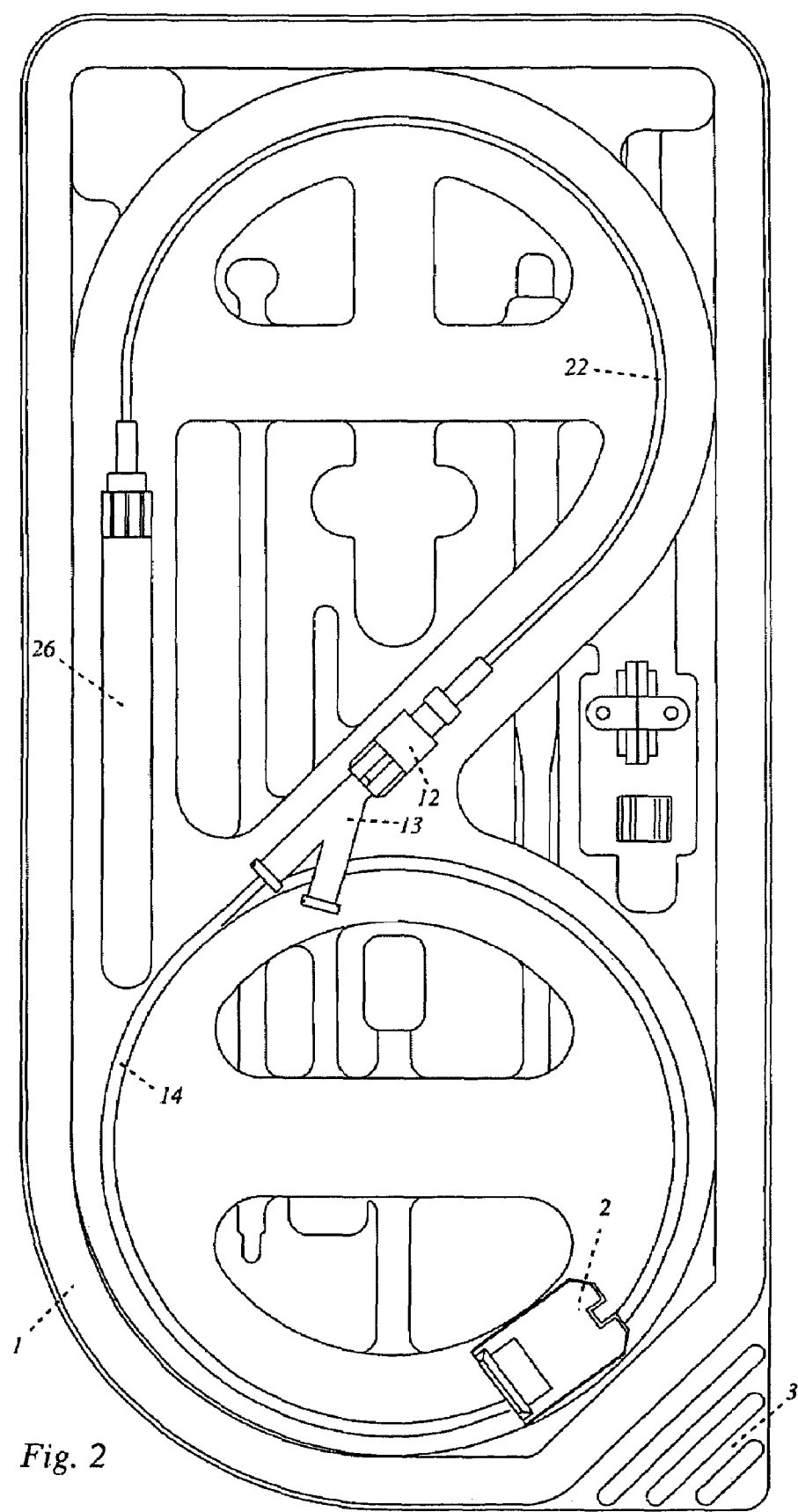
FIG. 2 shows a top view of a sensor arrangement according to the invention, having a blister pack that is completely opened, and in which the extravasal part of the sensor is laid as a loop which partially overlaps itself.

As shown in longitudinal cross-section in FIG. 1, the tube-like reflector insert 25 (made of extruded plastic such as silicone or polyurethane with a proportion of about 25% of filler such as barium sulfate), is located loosely in a rigid, light-absorbing sleeve 26 that is closed on one side, and forms the two-part reflector body with sleeve 26. A nut 24 with a Luer lock thread is glued onto the open side of sleeve 26. Reflector insert 25 is enclosed as a result. The intravasal part of sensor 11, which must be kept sterile, is guided in a protective tube 22 having Luer lock connector threads 21, 23 glued on both sides. Protective tube 22 is screwed onto Y connector piece 13 and reflector sleeve 26 with nuts 12 and 24 (releasable Luer lock connection).

The reinforced extravasal part 14 of the sensor is tightly glued into Y connector piece 13 with casting mass 15. Connector 16 can be used for infusions and for flushing. The tip of sensor 10 is inserted with slight play (shown in exaggerated manner) into the sensor cavity of reflector insert 25, essentially free of force. The play ensures that sterilization gas can reach all of the intravasal surfaces. The sterilizability can be slightly improved by means of a rough inside surface or a profiled sensor cavity in reflector insert 25. As long as the free length in the sensor cavity is more than twenty times the inside diameter of the latter, the insertion depth is relatively non-critical. The insertion depth is determined by the length of the protective tube 22. The attachment of the reflector to the sensor takes place by screw connection 12, 21 outside of the intravasal region. The position of the calibration reflector device (protective tube 22, reflector body 25, 26) relative to the sensor is fixed in place without exerting any harmful forces on the sensor: Screw connection 12, 21 ensures that the calibration reflector device is connected with the sensor without exposing intravasal sensor part 11 to clamping stress. Free access for sterilization gas is possible at all intravasal surfaces of the sensor.

In a partial region of the circumference, an interstice can be provided between reflector insert 25 and sleeve 26, in order to facilitate entry into the end region of sleeve 26 for sterilization gas, so that the gas can enter into the sensor cavity from two sides. This can be implemented in simple manner, for example by means of a groove provided on the inside of the sleeve and/or on the outside of reflector insert 25.

The sensor is assembled with protective tube 22 and reflector body, packaged into a blister pack 1, and gas-sterilized. After blister pack 1 is opened, the sensor is connected with an evaluation device (not shown) by way of a plug connector 2 affixed to extravasal part 14, which connector is clamped into blister pack 1 close to tear-open tab 3, and an essentially known one-point calibration is carried out with the calibration reflector device. Since intravasal part 11 of the sensor is protected from contamination by means of protective tube 22 and the reflector body, this can take place in a non-sterile environment. Only immediately before introduction of the sensor is screw connection 12, 21 loosened and protective tube 22 and reflector body 25, 26 are removed. The intravasal part of sensor 11 can be introduced into a catheter that is already present (e.g. central-venous) and screwed in place. The vascular access is maintained by connector 16.

Accordingly, while only a few embodiments of the present invention have been shown and described, it is obvious that many changes and modifications may be made thereunto without departing from the spirit and scope of the invention.

What is claimed is:

1. A calibration reflector device for a fiber-optic sensor, comprising:
    a rigid reflector body having a sensor cavity for accommodating a sensor end, said cavity being accessible from an access side at a first end of said rigid reflector body; and
    connection devices for reversibly connecting a connector piece to the access side, when said connection devices are in a locked position, said connection devices are disposed radially outside and around a free space wherein said free space is adjacent to said access side, for passing the sensor through, wherein a cross-sectional area of said free space is at least as large as a cross-sectional area of the sensor cavity.

2. A calibration reflector device according to claim 1, wherein the reflector body has an opaque sheathing and a reflector insert that is inserted into the sheathing, in which insert the sensor cavity is located.

3. A calibration reflector device according to claim 2, wherein the sheathing is black at least on an inside.

4. A calibration reflector device according to claim 2, wherein the reflector insert comprises a transparent plastic matrix and a filler.

5. A calibration reflector device according to claim 4, wherein the plastic matrix comprises polyurethane or silicone.

6. A calibration reflector device according to claim 4, wherein the filler comprises barium sulfate.

7. A calibration reflector device according to claim 1, wherein the sensor cavity has a textured surface on an inside surface.

8. A calibration reflector device according to claim 1, wherein said connection means is selected from the group consisting of a screw connection, a bayonet connection, snap-in means and clamping means.

9. A calibration reflector device according to claim 1, further comprising an extension piece disposed between the connection devices and the reflector body.

10. A calibration reflector device according to claim 9, wherein the extension piece is flexible at least in sections.

11. A calibration reflector device according to claim 1, wherein the sensor cavity has an axial length of at least thirty times the square root of its cross-sectional area.

12. A sensor arrangement comprising:
    (a) a fiber-optic sensor that has a flexible intravasal part and a rigid connector piece; and
    (b) a calibration reflector device that comprises the following:
        (i) a rigid reflector body that has a sensor cavity that accommodates an end of the intravasal part of the sensor, said cavity being accessible from an access side located at a first end of the rigid reflector body; and
        (ii) connection means for releasably connecting the connector piece of the sensor with the calibration reflector device,
        wherein the connection means is disposed radially outside and around a free space of the reflector device for passing the sensor through, the free space being disposed adjacent to said access side and having a cross-sectional area that is greater than a cross-sectional area of the intravasal part of the sensor, and wherein the intravasal part of the sensor has radial play in said sensor cavity.

13. a sensor arrangement according to claim 12, wherein the reflector body comprises a rigid sheathing that is opaque at least on a working wavelength range of the senor, and a reflector insert that is inserted into the sheathing, wherein said sensor cavity is located in said insert.

14. A sensor arrangement according to claim 13, wherein the sheathing is black at least on an inside.

15. A sensor arrangement according to claim 13, wherein the reflector insert comprises a transparent plastic matrix and a filler.

16. A sensor arrangement according to claim 15, wherein the plastic matrix comprises silicone or polyurethane.

17. A sensor arrangement according to claim 15, wherein the filler comprises barium sulfate.

18. A sensor arrangement according to claim 12, wherein the sensor cavity has a textured surface on an inside.

19. A sensor arrangement according to claim 12, wherein the connection means is selected from the group consisting of a screw connection, a bayonet connection, snap-in means and clamping means.

20. A sensor arrangement according to claim 12, further comprising an extension piece disposed between the connection means and the reflector body, wherein the sensor has radial play in the extension piece.

21. A sensor arrangement according to claim 20, wherein the extension piece is flexible at least in sections.

22. A sensor arrangement according to claim 12, wherein the intravasal part of the sensor extends into the sensor cavity such that the sensor cavity has a free length of at least ten times the square root of its cross-sectional area.

23. A sensor arrangement according to claim 22, wherein the intravasal part of the sensor extends into the sensor cavity such that the sensor cavity has a free length of at least twenty times the root of its cross-sectional area.

24. A sensor arrangement according to claim 12, wherein the intravasal part of the sensor extends into the sensor cavity at least 20 mm and at most 60 mm.

25. A sensor arrangement according to claim 12, wherein the intravasal part of the sensor is sterile, and the calibration reflector device is sealed to maintain the sterility of the intravasal part.

26. A sensor arrangement according to claim 12, wherein the connector piece of the sensor has a flushing opening.

27. A sensor arrangement according to claim 12, further comprising a blister pack encasing the sensor arrangement, said blister pack being openable without aids.

28. A sensor arrangement according to claim 27, wherein the blister pack has a tear-open point having a tear-open aid for tearing the blister pack open in a defined manner.

29. A sensor arrangement according to claim 28, wherein the sensor has a plug connector that is placed closer to the tear-open point than the sensor cavity.

30. A sensor arrangement according to claim 29, wherein the blister pack has a marking up to which the blister pack can be torn open in a defined manner to allow the plug connector to be removed while maintaining the intravasal part of the sensor in the blister pack.

31. A method for sterile packaging of a fiber-optic sensor arrangement, which comprises an intravasal part and a connector piece having a flushing connector, comprising the following steps:

providing a rigid reflector body that has a sensor cavity into which the intravasal part of the sensor can be introduced from an access side of a first end of said rigid reflector body, wherein a free space is disposed adjacent to said access side to allow radial play;

inserting a free end of the intravasal part of the sensor into the sensor cavity;

producing a releasable connection of the connector piece with the reflector body;

placing the sensor arrangement into a blister pack;

sterilizing the sensor arrangement with a sterilization gas after producing said releasable connection, and closing the blister pack.

* * * * *